(12) United States Patent
Wyatt et al.

(10) Patent No.: US 8,122,773 B2
(45) Date of Patent: Feb. 28, 2012

(54) SYSTEMS AND METHODS OF POWER OUTPUT MEASUREMENT

(76) Inventors: Roland Jeffrey Wyatt, Bozeman, MT (US); Dylan John Seguin, Berkeley, CA (US); Richard Benjamin Knapp, Sebastopol, CA (US)

( * ) Notice: Subject to any disclaimer, the term of this patent is extended or adjusted under 35 U.S.C. 154(b) by 375 days.

(21) Appl. No.: 12/543,023

(22) Filed: Aug. 18, 2009

(65) Prior Publication Data

US 2009/0308179 A1 Dec. 17, 2009

Related U.S. Application Data

(63) Continuation-in-part of application No. 11/380,945, filed on May 1, 2006, now abandoned.

(60) Provisional application No. 60/678,887, filed on May 6, 2005.

(51) Int. Cl.
*G01N 3/08* (2006.01)
(52) U.S. Cl. .............................. 73/818; 73/760
(58) Field of Classification Search ............ 73/760–818
See application file for complete search history.

(56) References Cited

U.S. PATENT DOCUMENTS

| 5,361,649 | A | * | 11/1994 | Slocum, Jr. | .............. | 74/594.2 |
|---|---|---|---|---|---|---|
| 5,836,094 | A | * | 11/1998 | Figel | .............. | 36/131 |
| 5,878,378 | A | * | 3/1999 | Brommer et al. | .............. | 702/139 |
| 6,196,084 | B1 | * | 3/2001 | Ueda | .............. | 74/594.6 |
| 7,072,789 | B2 | * | 7/2006 | Vock et al. | .............. | 702/141 |
| 7,503,133 | B2 | * | 3/2009 | Muraoka | .............. | 36/131 |
| 2006/0248965 | A1 | * | 11/2006 | Wyatt et al. | .............. | 73/862.391 |

* cited by examiner

*Primary Examiner* — Max Noori
(74) *Attorney, Agent, or Firm* — K. Karel Lambert; Lambert Patent Services, LLC (57) ABSTRACT

The present invention pertains to systems and methods for measuring power output, as in an athletic activity such as cycling. One embodiment relates to a force sensing device configured to be mounted on the bottom surface of a shoe as part of a mechanical linkage through which force is exerted. For cycling, the force sensor is mounted on the bottom surface of a cycling shoe and fitted with a cleat that interlockingly engages a bicycle pedal. To measure both positive and negative pressures on the pedal, the force sensor is pre-stressed with a compressive load to an intermediate point in its dynamic range. Strains that further compress or decompress the force sensor can thus be measured. The computing module mathematically converts the measured pressures, positive and negative, to a measurement of total power exerted by the rider. In addition, the computing module may utilize cyclical regularities in the signal to compute the rider's cadence (pedal revolutions per unit of time). Data from the force sensor is transmitted wirelessly to a remote display where it can be viewed by the rider.

15 Claims, 6 Drawing Sheets

SYSTEMS AND METHODS OF POWER OUTPUT MEASUREMENT

RELATED APPLICATIONS

This application is a continuation-in-part of U.S. patent application Ser. No. 11/380,945 filed May 1, 2006, which claims priority to U.S. Provisional Application Ser. No. 60/678,887 filed May 6, 2005.

BACKGROUND

1. Field of the Invention

The present invention relates to systems and methods of power output measurement. In particular the present invention relates to a power measurement device.

2. Background of the Invention and Related Art

Endurance athletes utilize various metrics to measure their performance and chart their workouts. These metrics are recorded and analyzed both during and after workouts. For example, interval type workouts typically involve multiple sets of intense activity, semi-intense activity, and rest. The intense activity may be characterized by a range of metrics which correlate to the desired intensity for a particular athlete. Likewise, the rest or semi-intense activity periods may be characterized by a range or metrics which correlate to the desired restful state for a particular athlete. One common form of metric measurement includes an athlete's heart rate. An athlete can utilize specific heart rate ranges to obtain desired intensity or restful states. Various well known methodologies exist for analyzing heart rate including the use of $VO_2$max, maximum heart rate, age, etc. However, it has been determined that heart rate alone is not necessarily an accurate assessment of the amount of work an individual is exerting at any given time. For example, as an athlete improves or increases fitness, his/her maximum heart rate may increase while relative working heart rate for a particular activity may remain constant. In this case, conventional heart rate measurement will not accurately identify an athlete's increased performance. Therefore, it is necessary to utilize other metric measurements or combinations of metrics to accurately measure an athlete's work load during a particular activity.

One particularly useful metric measurement involves calculating the amount of power or work an athlete generates or performs as a function of time. An increase in power output directly translates to an increased athletic performance. Likewise, a decrease in power output translates to a decreased athletic performance. The measurement of instantaneous power has become popular for certain activities, including cycling. Power output has been determined to be a more accurate measurement of an athlete's performance and is therefore a more useful metric for analysis and improvement. Power is a function of force, and many sports involve the application of force in a variety of directions.

Unfortunately, it is difficult to accurately measure an athlete's total or instantaneous power output. While force sensors have been used for a variety of purposes, there are difficulties in adapting this technology to power monitoring in athletics. For example, U.S. Pat. No. 5,471,405 to Marsh uses a pair of sensors, one in each shoe of a wearer. Pressure on the sensor is digitized and transmitted wirelessly to a microprocessor with display, also worn by the wearer, so that the user can monitor a "force envelope" associated with each stride or jump. Marsh teaches that the weight of the user must be known to calibrate the output. The measured force goes to zero when no weight is applied. Marsh further teaches that the force sensor should not carry the entire pressure of the wearer's weight, but rather a representative amount, so that an approximation of output can be calculated using a proportionality constant that would likely vary with stance. However, this information is not sufficient for accurately quantifying power output and is merely an indication thereof.

In cycling, others have attempted to calculate power output as a function of pedal cadence or wheel revolution, chain tension, or axial strain around the crank or rear wheel hub, for example. Patent literature directed at this problem includes for example U.S. Pat. Nos. 4,423,630 to Morrison, 4,430,800 to Shimano, 5,031,455 to Cline, 5,065,633 to Mercat, 5,154,677 to Ito, 5,167,159 to Lucking, 5,257,540 to Bower, 6,356,848 to Cote, 6,418,797 to Ambrosina, U.S. Pat. No. 7,257,468 to Costa, and associated references.

However, none of the references cited contemplate using force sensing resistors to measure total energy consumed by an athlete by first pre-stressing a force sensor between the pedal or cleat and the foot so that both push and pull strains on the sensor can be integrated into the total force output measurement. This is of particular interest to bicyclists, where the legs alternate between flexion and extension during pedaling, and the bicyclist may apply a power stroke in both flexion and extension on each pedal, for example.

Rotational velocity devices for use in bicycling include the Mavic (Annecy, France) Wintech (which uses a magnet mounted on the spokes and a Hall effect sensor to measure rotational speed). This measurement scheme is inherently inaccurate because the power necessary to pedal at a particular cadence or wheel speed depends tremendously upon the surface over which the bicycle is traveling. For example, a steep hill requires more power per pedal stroke than a flat or downhill grade. Likewise, systems that attempt to extrapolate power measurements from heart rate or opposing forces are inherently flawed because they do not account for the increased power output that often accompanies an increase in fitness.

Systems for bicycles such as the Powertap (Saris, Madison Wis.) rely on a hydraulic sensor mounted in the hub of the rear wheel and thus measure only power at the wheel, not the full power exerted at the crank. The modified hub alone weighs over 500 grams, a disadvantage in competition. Power meters manufactured by SRM (Julich, Del.) operate at the crank, again adding extra weight, and not measuring power directly at the mechanical linkage between the user's leg and the pedal, where any inefficiency is wasted. While crank-positioned power meters measure more power than those positioned at the hub, these systems are also very expensive.

Accordingly, there is a need in the art for a system of power output measurement that provides a more complete and accurate assessment of the total forces exerted by the athlete, such as a cyclist.

SUMMARY OF THE INVENTION

The present invention pertains to systems and methods of individual power output measurement. One embodiment relates to a pressure sensing device configured to be mounted on the bottom surface of a shoe. The device includes a sensor, a wireless communication system, and a mounting system. A second embodiment relates to a direct power measurement system including a pressure sensing device, a computer module, and a display module. In a bicycling application of the system, the device is mounted on the bottom surface of a shoe so as to measure applied pressure between at least one of the rider's shoe and corresponding bicycle pedal. The computing module mathematically converts the measured pressure as a function of time to a value of power exerted by the rider. In addition, the computing module may utilize variations in the measured pressure as a function of time to compute the rider's cadence (pedal revolutions per unit of time). Various well-known communication systems such as RF may be integrated within the device and computing module to facilitate data transmission.

The force sensor is mounted in a mechanical linkage between a shoe (as driver member) and a cleat and pedal (as driven member) wherein the driven member is connected to a crank and a drive train; and the shoe is worn by a user. A force sensor having an output analog signal, is interposed in the mechanical stack or linkage between the driver member and the driven member, forming a load cell that directly transmits power applied by the driver member to the driven member. The output analog signal of the force sensor varies with the load applied by the user to the pedal through the shoe.

In pedaling a bicycle, a cleat attached to the rider's shoe may be configured to engagingly interlock with the pedal so that power may be applied both as a down-stroke and an up-stroke. Advantageously, in order to measure power expended in both the down-stroke and the up-stroke (which involve both flexion and extension of muscle groups), we have discovered that by pre-loading the force sensing transducer with a static compressive load to an intermediate point in the dynamic range of the sensor, then the sensor can measure both down-stroke "positive" and upstroke "negative" dynamic load pressures applied thereon and thus more accurately monitor total power output by the user.

These and other features and advantages of the present invention will be set forth or will become more fully apparent in the description that follows and in the appended claims.

BRIEF DESCRIPTION OF THE DRAWINGS

In order that the manner in which the above-recited and other advantages and features of the invention are obtained, a more particular description of the invention briefly described above will be rendered by reference to specific embodiments thereof which are illustrated in the appended drawings. Understanding that these drawings depict only typical embodiments of the invention and are not therefore to be considered limiting of its scope, the invention will be described and explained with additional specificity and detail through the use of the accompanying drawings in which.

DETAILED DESCRIPTION OF THE PREFERRED EMBODIMENTS

The present invention pertains to systems and methods of individual power output measurement. One embodiment relates to a pressure sensing device configured to be mounted on the bottom surface of a shoe. The device includes a sensor, a wireless communication system, and a mounting system. A second embodiment relates to a direct power measurement system including a pressure sensing device, a computer module, and a display module. In a bicycling application of the system, the device is mounted on the bottom surface of a shoe so as to measure applied pressure between the rider's shoe and the bicycle pedal. The computing module mathematically converts the measured pressure, both positive and negative, as a function of time to a value of power exerted by the rider. In addition, the computing module may utilize the measured pressure as a function of time to compute the rider's cadence (pedal revolutions per unit of time). Various well-known communication systems such as RF may be integrated within the device and computing module to facilitate data transmission. Similar systems may be used to calculate an individual's power output during other activities including but not limited to running, rowing, walking, cross-country skiing, and so forth. A third embodiment relates to a method for calculating individual power output during an athletic activity. The method includes sensing pressure at a particular location, calculating or computing power, and displaying power, where the pressure sensing device is pre-stressed and is configured to measure both positive and negative pressures. While certain embodiments of the present invention are directed at systems and methods of power output measurement for use in bicycling, it will be appreciated that the teachings of the present invention are applicable to other sports.

The following terms are defined as follows:

Metric—A numerical value relating to a particular measurement. For example, speed, heart rate, power output, cadence, stroke, etc. Power output may be measured in Watts, horsepower or calories per minute, for example.

Pressure Sensor—A device configured to measure the amount of applied pressure at a particular point or area, wherein the measured pressure is converted into an electrical analog signal. Pressure may be "positive" or "negative", corresponding to the vector of a force applied to a sensor, where a compressive load corresponds to a positive pressure and a decompressive load corresponds to a negative pressure-relative to a resting condition where no external load is applied. Thus the sensor of the invention is more generally termed a "force sensor" or "force transducer", where force is independent of direction. Preferred pressure sensors are "force sensing resistors", such as selected from those disclosed in U.S. Pat. Nos. 4,314,227, 4,314,228, 4,489,302, 5,296,837, and 5,302,936, for example, which may be formed as sheets of material with contact leads for sensing a force and generating an analog electrical signal in response thereto. Force transducers relying on resistive, capacitive or inductive effects are known and are termed here generally "force sensing resistors" (FSR).

Shoe—An article that covers a user's foot and possibly a portion of a user's lower leg. A shoe may be composed of both flexible and rigid materials and combinations thereof. A shoe may be designed to achieve specific performance characteristics consistent with a particular sport. For example, a cycling shoe is generally rigid so as to maximize force transfer between a rider and a bicycle.

Wireless communication system—Any system capable of transmitting data wirelessly between two or more points. For example, a radio transmitter may be used to convert and transmit electrical signals across a radio frequency to a radio receiver.

Mounting system—An attachment system for mechanically coupling one item to another. For example, a mounting system is used in accordance with embodiments of the present invention to couple a pressure sensing device to a user and/or an athletic article.

Figure 1:
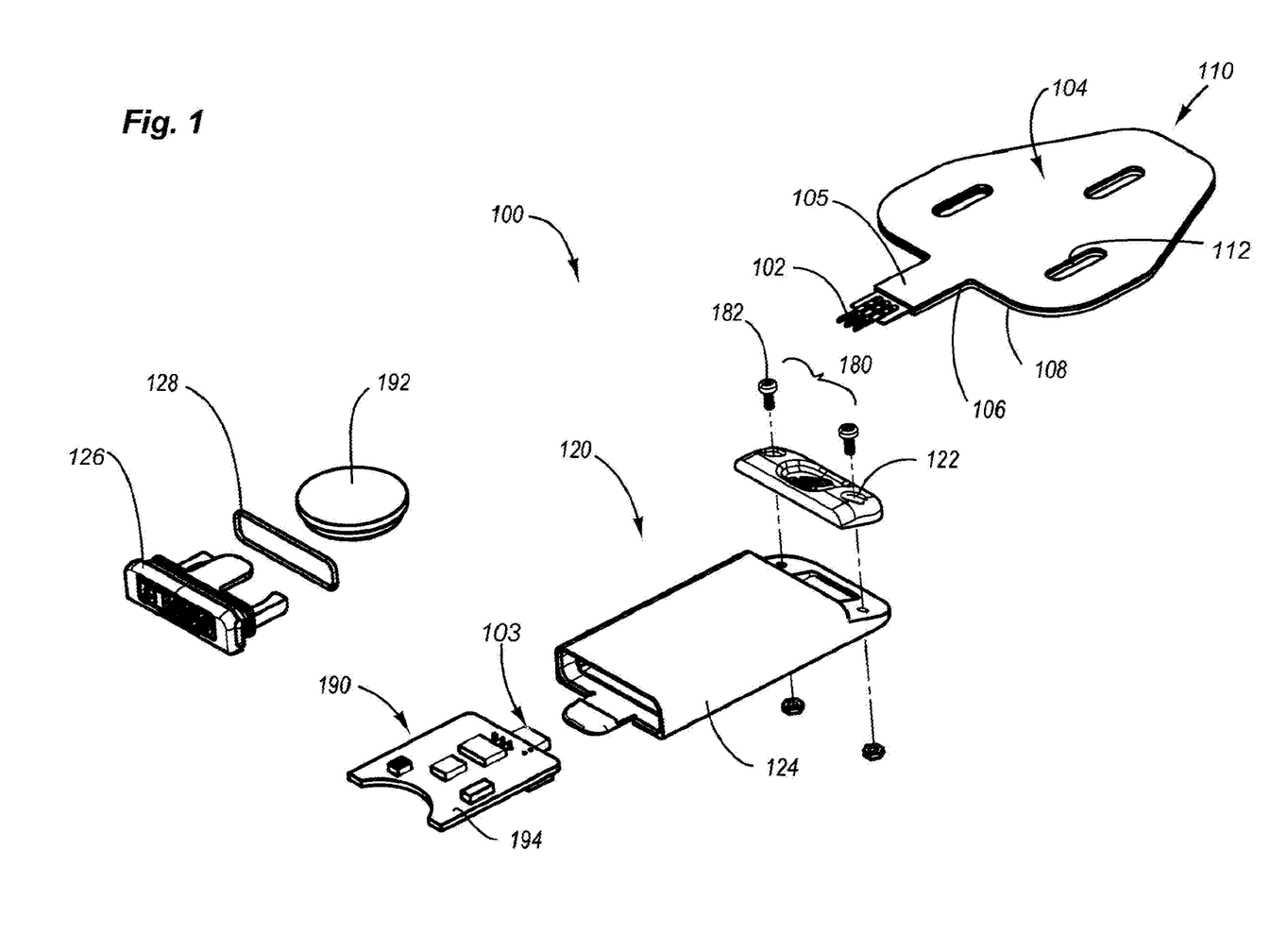
FIG. 1 illustrates an exploded view of a pressure sensing device configured to be mounted on a shoe in accordance with one embodiment of the present invention.

Reference is initially made to FIG. 1, which illustrates an exploded view of a pressure sensing device configured to be mounted on a shoe in accordance with one embodiment of the present invention, designated generally at 100. The pressure sensing device 100 includes a sensor sub-assembly 110, a wireless housing assembly 120, a wireless communication system 190, and a junction plate mounting system 180 with junction cover 122 and mounting hardware 182. The sensor assembly 110 includes a sensor coverplate 104, a sensor baseplate 108, with the force sensor layer 106 itself sandwiched between the top and bottom sensor housings. Sensor tongue 105 with electrical coupling 102 is for linking the sensor layer 106 with a power supply and detector circuit via wireless communication circuitry 190 as will be explained below. Sensor coverplate 104 is intended to contactingly engage a cleat attached thereto; sensor baseplate 108 is intended to contactingly engage the sole of a shoe on which it is mounted.

Figure 3:
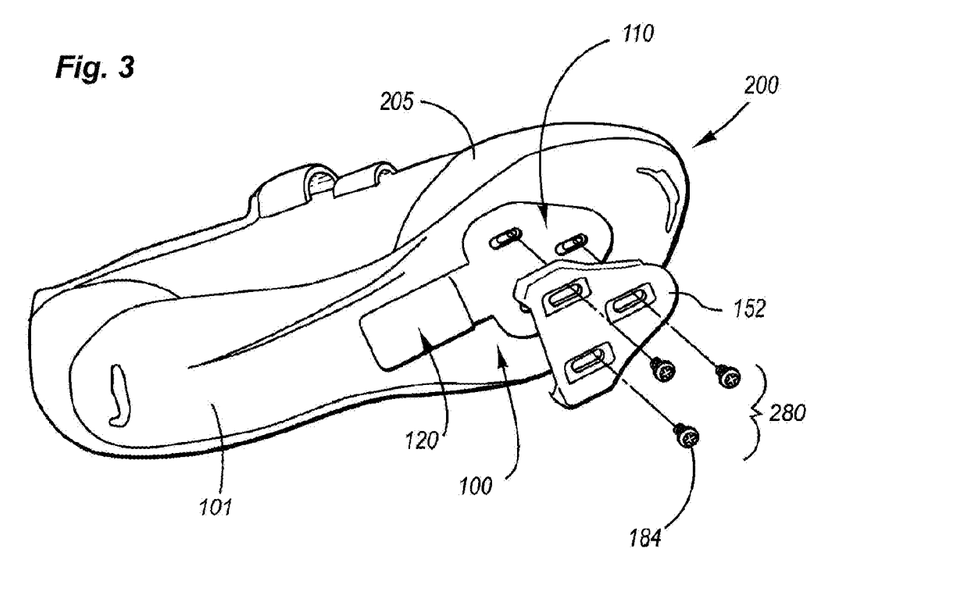
FIG. 3 illustrates a perspective view of the bicycling shoe of FIG. 2, further illustrating the exploded attachment of a sensor device with cleat.

The sensor assembly 110 further includes a plurality of holes 112 which serve as part of the sensor mounting system 280, as illustrated in FIG. 3. The holes 112 may be arranged to be consistent with a universal 3-hole Look™ style "mounting interface" on the sole of the shoe. Fasteners 184 secure the sensor assembly 110 to the shoe.

The illustrated force sensor layer 106 includes a force sensing resistor (FSR). Force sensing resistors are uniquely suited for athletic force measurement due to their dimension and weight characteristics. The electrical resistance at the electrical coupler 102 of the sensor layer 106 is directly related to the amount of pressure or force applied. Force sensing resistors may be resistive, capacitive or inductive, as would be known to those skilled in the art. More recently, a newer force sensor material formed of a piezoresistive rubber has become available and is also suitable for use here. The force sensing resistor element 106 is formed generally as a sheet in the shape of the sensor housing members 104, 108 and forms a thin layer therebetween.

The wireless and battery housing assembly 120 is configured to protect portions of the device that may otherwise be damaged by exposure or incidental contacts. The illustrated housing assembly 120 includes an enclosure or shell 124, a junction cover 122, an o-ring 128, and a cover 126. The enclosure 124 provides a cavity in which portions of the wireless communication system 190 may be housed. In addition, the junction plate mounting system 180 and housing enclosure 124 form a seal around electrical connection 102. The o-ring 128 and cover 126 form an access panel on the back of the enclosure 124. The access panel allows the user to replace the battery, and check or repair printed circuit board 194.

The wireless communication system 190 is electrically coupled to the sensor 110 via electrical coupler 102 at junction 103. The wireless communication system 190 is configured to wirelessly transmit data corresponding to the pressure applied upon the sensor 110. The illustrated wireless communication system 190 further includes a printed circuit board 194 and a power supply 192. The power supply may include batteries that are optionally configured to be rechargeable without removal from the device 100. The printed circuit board 194 includes electrical components including but not limited to a transmitter, an antenna, a processor, and an A/D converter, as needed. The printed circuit board 194 may further include a microprocessor that performs one or more mathematical computations on the measured pressure such as a mathematical conversion to quantify power or adds a unique identifier to the wireless output data for distinguishing signals. The transmitter may be configured to transmit the data utilizing any wireless data medium including but not limited to radio frequency, microwave, magnetic coupling, infrared, etc. In addition, the power supply 192 and corresponding circuitry on the printed circuit board 194 are arranged in a manner that will also conform to the internal dimensions of the housing 124.

Figure 2:
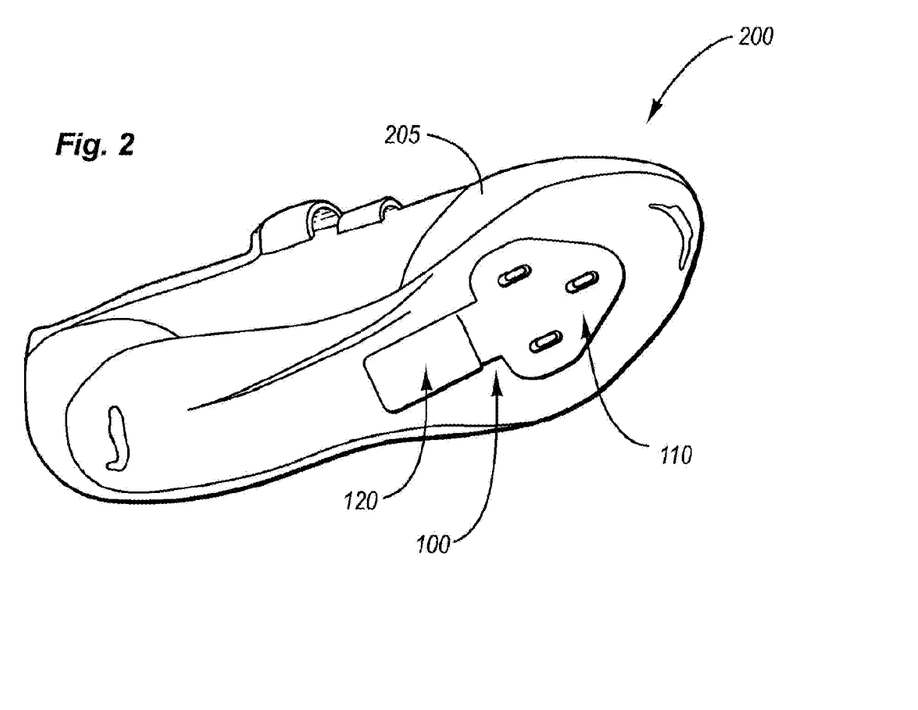
FIG. 2 illustrates a perspective view of a bicycling shoe with a pressure sensing device attached in accordance with a power output measuring system embodiment of the present invention.
Figure 4:
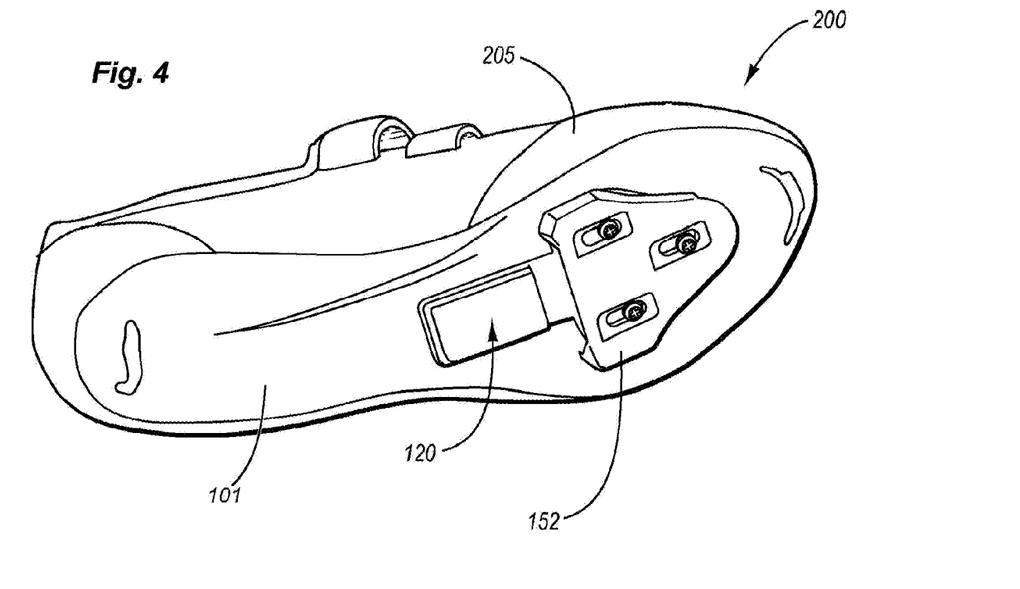
FIG. 4 illustrates a perspective view of the fully assembled pressure sensing device and cleat illustrated in FIGS. 2 and 3.

Reference is next made to FIGS. 2-4, which illustrate a perspective view of a biking shoe with a pressure sensing device attached in accordance with a power output measuring system embodiment of the present invention, designated generally at 200. The illustrated shoe 205 is a cycling shoe, and the illustrated pressure sensing device 100 is the pressure sensing device 100 described with reference to FIG. 1. A preferred bicycling shoe has a generally rigid sole 101 and is designed to accept a "cleat" 152 for engaging the pedal of a bicycle. The cleat 152 is shaped three dimensionally to contactingly engage the sensor coverplate 104. In addition, the cleat 152 includes a plurality of holes positioned to correspond to the holes of the sensor 110. Three attachment members 184 may then be extended through the sensor cover 152, the sensor 110, and into a receiving boss on the shoe 205 as part of the sensor mounting system 280. Various seals, boots, gaskets or couplers may also be utilized to prevent water or debris from contacting the sensor at the seams around the sole or cleat.

It should be noted that the cleat 152 must be coupled to the shoe 205 in a manner that allows for effective force transfer to the sensor assembly 110 and force sensing layer 106. The sole, sensor, and cleat combination form a stacked mechanical linkage joining the athlete with the pedal of the bicycle. The position of the linkage at the ball of the foot, along with the structure of the stacked components, ensures that all forces expended by the rider on the pedals are transmitted through that mechanical linkage, independent of the vector of the forces. The force sensing layer is designed with shape and surface area to be interposed between the driving shoe and the cleat/pedal and to form a contacting layer therebetween through which all forces are transmitted. Because the cleat is designed to engagingly interlock with a mating surface on the pedal, the wearer has the option of pushing down on the pedal or pulling up on the pedal during each cycle to exert force. The cyclist may exert energy on the pedal during flexion involving the hamstrings or gastrocnemius muscles, or on extension using the quadriceps of the thigh. A racing cyclist may do both, applying energy with the right and left legs simultaneously on flexion and extension during each turn of the crank. Thus the energy of the cyclist is measured not only as downward "positive" pressure on the pedals to turn the crank during a first half cycle, but also as upward "negative" pressure on the pedals during a second half cycle. Both positive and negative pressure (force) are converted to work on the pedals, and a complete measurement of the work output of the cyclist is a summation of all the forces exerted on the pedals, independent of the vector of the forces.

Figure 5:
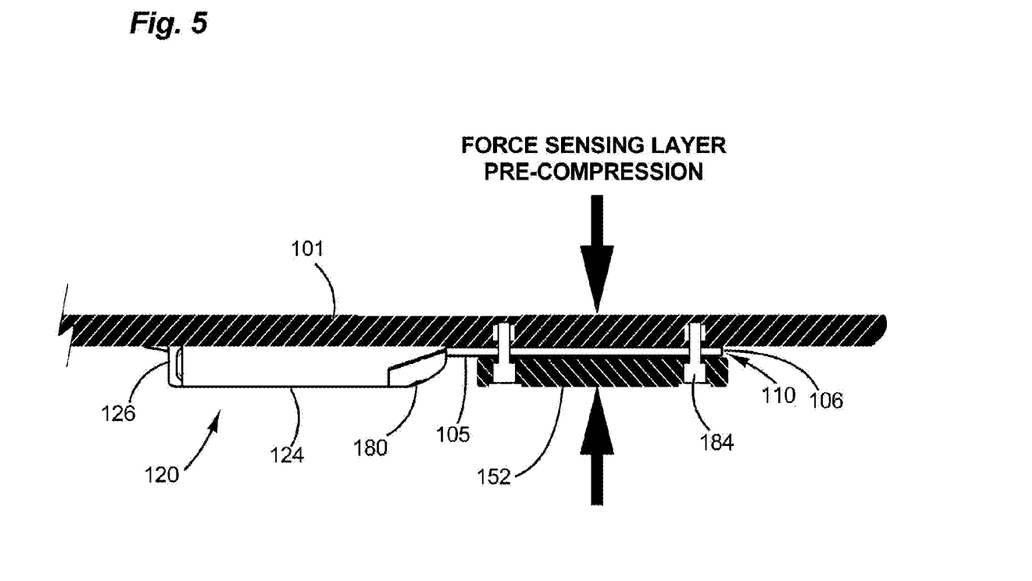
FIG. 5 illustrates a schematic view of the assembled pressure sensing device of FIG. 4, showing the pre-loading of the force sensing resistor.

Turning to FIG. 5, we see how both pushing "positive" and pulling "negative" forces may be measured by the invention. Departing from customary practice, we pre-stress the force sensing layer 106 by applying a static load on the pressure sensor sandwich in the load cell, compressing together the bottom baseplate 108 and the cleat 152 (which is operatively coupled to the top coverplate 104) against the sole 101 by applying torque to the fasteners 184. By pre-adjusting the torque on the fasteners, a dynamic range is achieved which spans both compression of the sensor layer 106 and decompression of the sensor layer 106 by the end user, the compression corresponding to a pushing load applied downward on the pedal (in extension), and the decompression corresponding to a pulling load applied upward to the pedal through the cleat (in flexion), which is interlockedly engaged with the pedal during cycling. The shoe with sole is the driving member, and the cleat (or pedal) is the driven member, which in turn engages the crank and drive train, but the shoe can drive the pedal both up and down by applying positive or negative force to the pedal through the cleat.

As seen in side view, the device is mounted on the sole 101 of a shoe. The cleat 152 is threadingly affixed to the sole 101 by fasteners 184. Between the cleat and the sole, the sensor assembly 110 with FSR layer 106 is sandwiched. The fasteners 184 are torqued to a predetermined setpoint so as to statically bias the resistance of the FSR layer. The resting voltage drop across the FSR layer is adjusted in this way so that deformation under compressive load results in less resistance and deformation under decompressive load results in greater resistance. The resting voltage drop is not zero. The dynamic range thus spans negative and positive loads on the sensor assembly 110 with force sensor layer 106.

Seen heelwise on the sole, the wireless and battery housing assembly 120 is connected to the sensor assembly 110 at tongue 105. As shown, the toe-end is to the left and the heel-end is to the right. It can be seen that the load cell covers the entire interface of the contact area between the shoe sole and the cleat. The cleat in turn interlockingly engages the pedal (not shown). The cleat is configured for engagingly interlocking at the pedal to the drive train of the bicycle so that both positive and negative pressure can be applied to the pedal. Thus any change in analog signal from the force sensor, when pre-compressed as shown, is a full measure of the entire force on the crank, not a partial measure.

The device is affixed to the sole 101 with two attachment members 182 configured to extend through a portion of the housing 120 and three attachment members 184 (illustrated in FIG. 3) which extend through a pedal interface member or "cleat" 152 and through the sensor 110 for attachment to the shoe. An adhesive coupling system may be used in place of or in conjunction with the attachment members 182. Various other mounting systems may be used in accordance with the present invention including quick-release type systems that would allow for efficient attachment and release of the device 100 to an article.

Construction assembly and materials may be varied. In some embodiments the sensor assembly is incorporated on the bottom surface of the cleat 152 or pedal interface member. The cleat body may replace the sensor baseplate 108, or alternatively the shoe sole may replace and substitute for the sensor coverplate 104. In other embodiments, the sensor assembly is built into the sole of the shoe. Optionally, the wireless and battery housing may be built or molded into the sole of the shoe, or similarly, with suitable miniaturization, into the cleat or other interface member. While the Look™ mounting system is used here for illustration, other configurations of fasteners may be used, as would be apparent from the teachings of the present invention. Two hole mounting systems are also useful. Other athletic article and pressure sensing device combinations may be practiced in accordance with the present invention.

Figure 6:
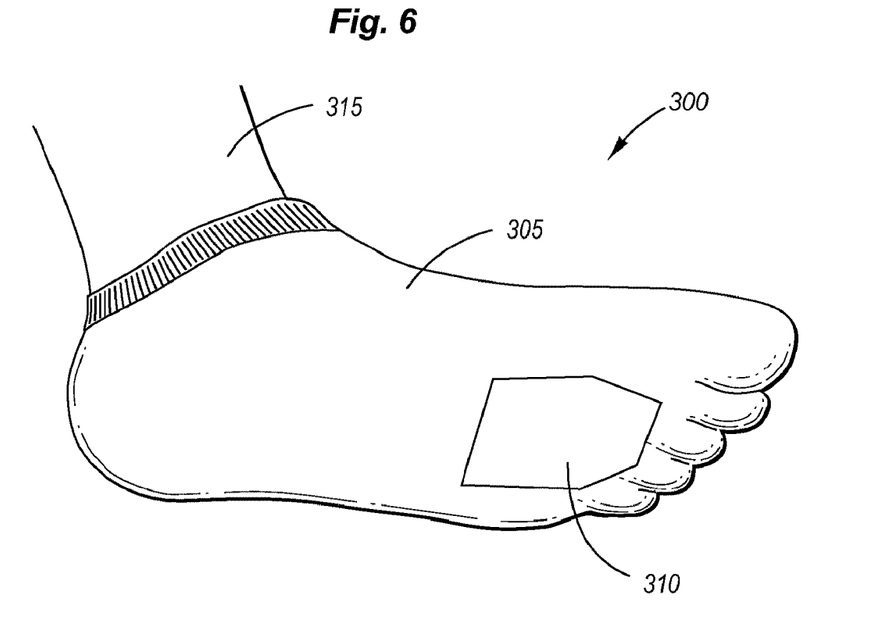
FIG. 6 illustrates a perspective view of a miniaturized pressure sensing device incorporated into a sock in accordance with an alternative device embodiment of the present invention.

Reference is next made to FIG. 6, which illustrates a perspective view of a pressure sensing device 310 incorporated into a sock 305 in accordance with an alternative device embodiment of the present invention, designed generally at 300. The sock 305 is an alternative article which may be used for attachment of a pressure sensing device 310 in accordance with the systems and methods of the present invention. Various sports such as cycling, running, etc. require athletes to exert forces by their feet onto the ground or another athletic article such as a bicycle pedal. Therefore, the measurement of pressure at the bottom of a user's leg 315 may be applicable in determining power output during particular athletic activities. The pressure sensing device 310 is positioned at approximately the ball of the user's foot for the most efficient measurement of exerted forces by a user. In addition, the bottom of the sock 305 may include a rigid or semirigid surface to assist in coupling and stabilization of the pressure sensing device 310 in relation to the remainder of the sock 305. As above, the sensor layer is pre-stressed and sandwiched between a rigid coverplate and a baseplate. A segmented force sensing layer may also be used for greater flexibility. Various pressure sensing devices 310 may be used in conjunction with a sock including but not limited to the pressure sensing device illustrated and described with reference to FIG. 1.

Figure 7:
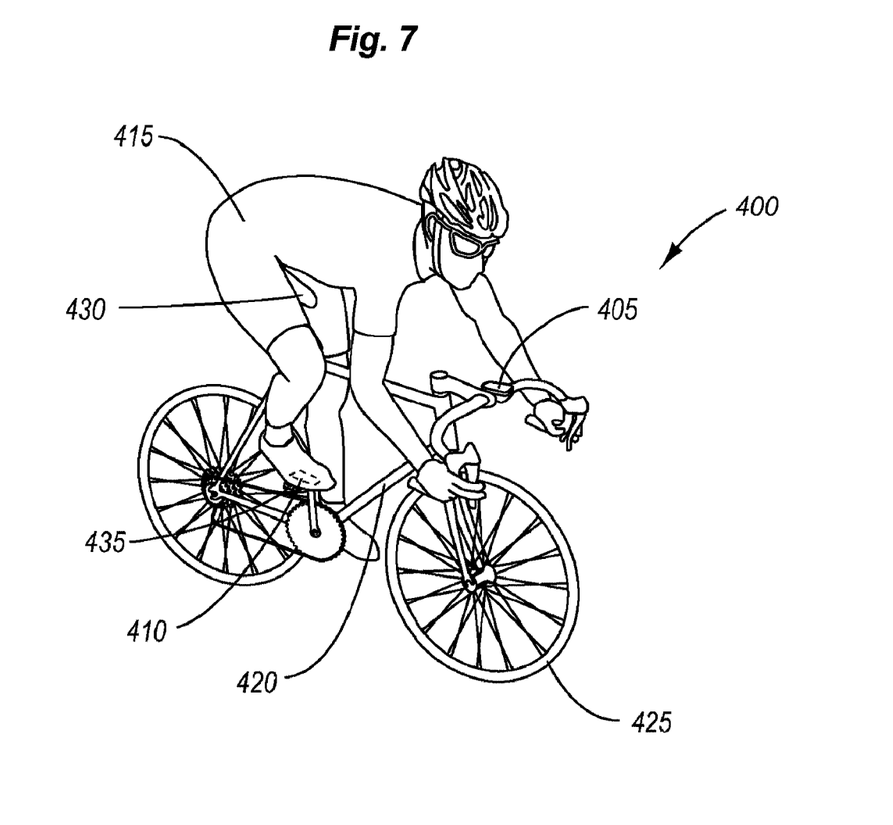
FIG. 7 illustrates a perspective view of one embodiment of a power output measuring system for a bicycle.

Reference is next made to FIG. 7, which illustrates a perspective view of one embodiment of a power output measuring system for a bicycle, designated generally at 400. The power measurement system includes pressure sensing devices 410 and a computing and display module 405. The pressure sensing devices 410 are positioned in a particular location between the rider 415 or user's shoe and the pedals of the bicycle, forming an element of a mechanical linkage therebetween. This location has been determined to effectively measure pressure for purposes of calculating power output of the user while cycling. The bicycle further includes a frame 420, two tires 425, a seat 430, and a pair of pedals 435. The pressure sensing devices 410 wirelessly transmit data to the computing and display module relating to the pressure and/or power output applied at each of the pressure sensing devices 410. It should be noted that alternative embodiments may utilize a single pressure sensing device 410 between only one of the rider's 415 shoes and pedal 435. The computing/display module 405 is positioned on the handlebars of the bicycle or other non-rotating surface, but may also be positioned on the user's wrist, on a cap or headband, or on the bicycle frame to allow for efficient visual recognition by the user. The computing/display module 405 calculates power output of the user while cycling by receiving data from the pressure sensing device or devices 410 and converting or computing power in a display format such as a numerical metric or visual graph. While not shown, it has been determined experimentally that the pressure measurements at the particular locations exhibit a cyclical characteristic that is consistent with the pedal cadence and can therefore be used to calculate and display cadence in addition to power output. Although illustrated for purposes of measuring a cyclist's power output, the teachings of the illustrated system are applicable to other athletic activities.

Figure 8:
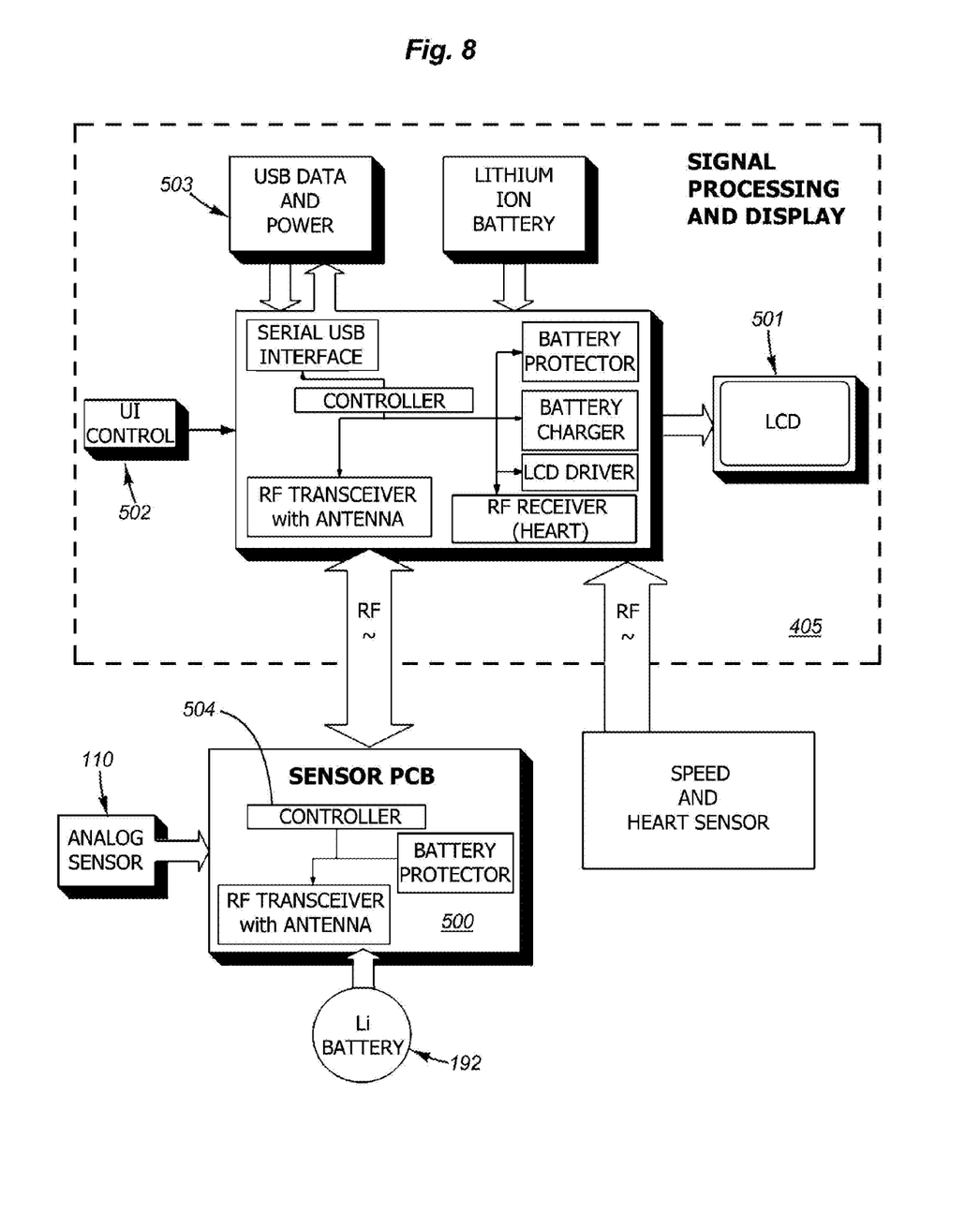
FIG. 8 illustrates a first embodiment of an operative block circuit diagram for measuring and displaying output of a pressure sensing device of the invention to a wearer.
Figure 9:
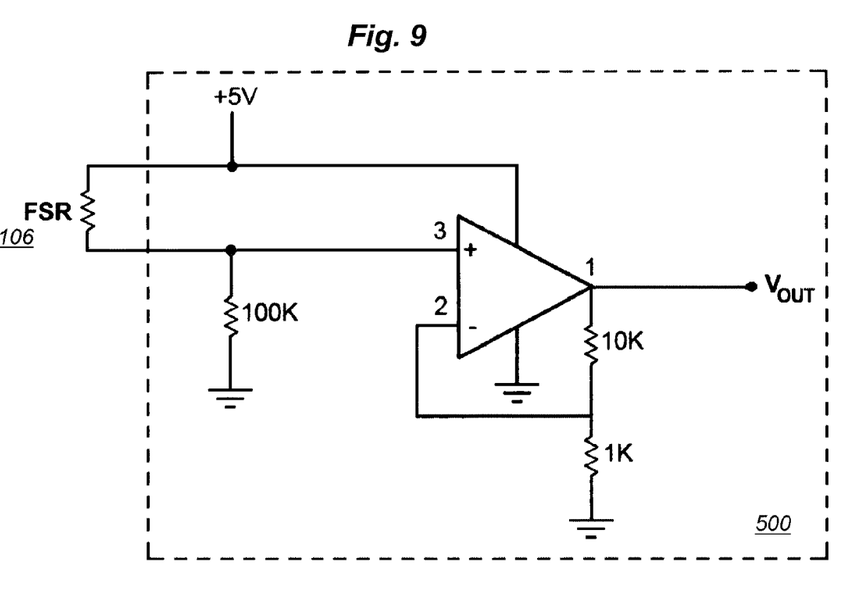
FIG. 9 further illustrates a circuit for sensing a pressure, here a partial view of the sensor PCB with attached analog sensor FSR. The analog sensor is pre-stressed so that the voltage output of the circuit at rest (with no external load) is a non-zero voltage.

Turning to FIG. 8, described schematically is a circuit for processing force data received from the sensing layer outlets 102. These circuits, and the sub-circuit of FIG. 9, are described for demonstration purposes and the invention is not limited thereto. The analog sensor 110 is powered by power supply 192. Positive or negative pressure applied to the FSR sensor 110 modulates the output voltage, which is amplified by a standard op-amp amplifier on sensor PCB 500 as illustrated in FIG. 9. The amplified output voltage $V_{OUT}$ from the sensor is split into three streams that are supplied to a microcontroller. The first stream is used to compute RMS, the second stream to generate a pulse stream that is proportional to the frequency of pulses in the output voltage (for determining cadence), and the third stream is directly transmitted to the microcontroller as a DC voltage. The microcontroller samples the three streams every $\frac{1}{10}$th of a second and counts the number of pulses that occur every second after a sensed pressure. This data is then buffered as 10 bit data in this example, and wirelessly transmitted using a Zigbee™ standard, or other wireless RF standard, to a signal processing and display unit 405. A transceiver module with antenna may receive the signal and drive a graphical display of the data on an LCD display screen 501. A user interface 502 may be provided if desired. The transceiver module may also be configured to receive multiple signals from a plurality of pressure sensing devices. Likewise, the wireless components may form a mesh network that allow for various devices to interface with one another. In addition, the receiver module may be equipped with a USB microcontroller and interface 503 to facilitate transferring data to a personal computer. Various other electrical configurations may be utilized in accordance with the present invention. Other signals, such as heart rate and speed, may also be processed by this circuitry. Optionally, cell phone transmittal protocols may also be used.

Sensor circuit 500 is configured for converting the measurement of the power expended to a digital signal and for wirelessly transmitting it to a signal processing and display circuit 405, or to a remote workstation, where it can be viewed by the athlete or by a coach. To zero the force measurement circuit, external loads are removed and the controller 504 establishes a set point. At this setpoint, the voltage output of the FSR 106 is a positive value determined by the torque on fasteners 184, for example 15-20 nM. Forces applied to the sensor are then sensed as changes in voltage from the non-zero setpoint and are converted by the controller 504 to a measurement of power.

Also provided is an optional method of dynamically bracketing a metric during an athletic activity. An athlete who is performing an athletic activity may often wish to hold a metric within a particular range so as to maximize performance. However, this range may not be quantifiable before or after the athletic activity. Therefore, it may be useful to dynamically bracket at least one metric associated with the athlete's athletic performance or exertion level. For example, heart rate and power output may be continuously monitored and displayed to the athlete. Upon recognition of a useful situation, the athlete makes a bracket request to a computer module. The method then assigns a bracket or set of metric values corresponding to a set of values substantially centered around the measure metric value at the particular time at which the bracket request was received. Various well known electrical systems and methods may be employed in the execution of this method in accordance with the present invention. Similarly, a target value of a metric can be set, either high or low, and an alert can be sent to the wearer when the target is reached.

Figure 10:
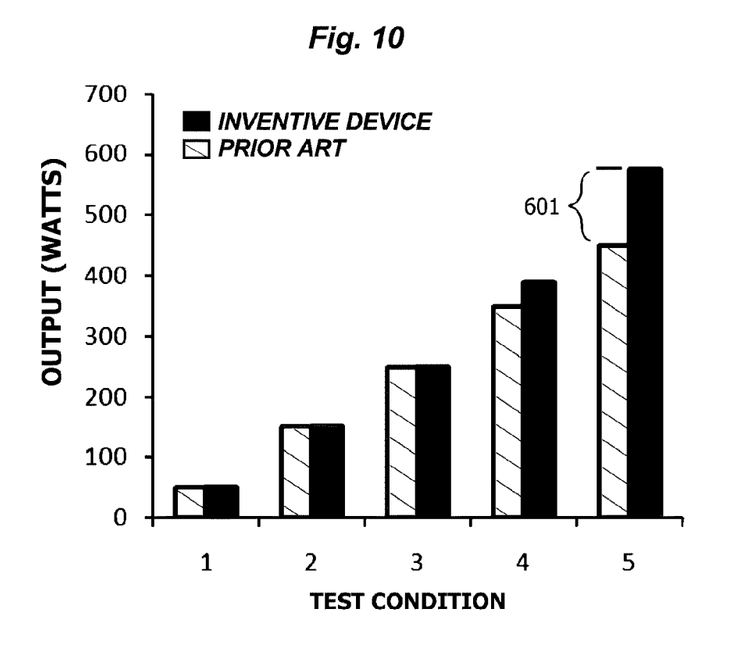
FIG. 10 shows data measured with a pressure sensing device of the invention under five conditions, and comparing the output with that of a competitive system.

FIG. 10 depicts comparative data obtained with the force sensor assembly of the present invention. A stationary bicycle was fitted with a Powertap rear wheel hub with power sensor (Saris, Madison Wis.). The rider was fitted with shoes having the inventive device of FIGS. 1-4. Both power monitoring systems were activated while the rider worked the bike. In this series, the rider was asked to pump with stepwise increases in power (measured in Watts) against stepwise increases in resistance. The results are plotted as paired data where the powertap data is shown as a hatched bar and the inventive device data is shown as a solid bar. Surprisingly, it can be seen that output from the inventive device was in close agreement at the lower end of the range, but above 300 Watts, the inventive device reports higher power output versus the Powertap. We interpret this to indicate that the inventive device is capturing a component of total power output that is not measured by the prior art device. Under more demanding conditions, the rider is apparently less efficient, exerting more energy to achieve the expected result. The inventive device is directly measuring power at the mechanical linkage between the rider's foot and the pedal of the crank; the Powertap is indirectly measuring power transmitted to the wheel. While not bound by theory, the difference 601 in power output is the inefficiency of coupling between the rider's musculature and the drive train through the wheel. Positioning the power measuring device at the linkage point between foot and pedal is thus more effective in measuring total power expended than at the wheel hub. To our knowledge, this is the first report of a device successfully used to measure this difference.

Interestingly, this raises the possibility that a training regime could employ two such power monitoring devices, one to measure power in the drive train and the other to measure power at the pedals. This would allow athletes to optimize their body motions while directly monitoring any inefficiencies in the coupling of foot, pedal and drive train.

More generally, the invention is a power monitor for measuring athletic activity, which comprises: a mechanical linkage for linking a driver member and a driven member, wherein the driven member is connected to a crank or reciprocating arm and a drive train; and a force sensor layer, the force sensor layer having an output analog signal, wherein the force sensor layer is interposed in the mechanical linkage, thus forming a contacting surface or interface between the driver member and the driven member; further characterized in that the force sensor layer is pre-stressed with a static compressive load, such that a deformation of the force sensor layer under a dynamic compressive load is detected as a positive change in the output analog signal and a deformation of the force sensor under a dynamic decompressive load is detected as a negative change in the output analog signal, the output analog signal at rest being non-zero. In a preferred embodiment, the driving member is a shoe, more generally termed here "driver member" or "driver shoe member" and the driven member is a cleat, more generally termed here "driven member". Yet more generally, the driving member may be a body part, such as the sole of a foot and the driven member is a member attached to the side of the force sensing layer opposite the driver member, such as a pedal or footpad. In another embodiment, the force sensing layer may be attached to or built into the pedal member, directly or indirectly, optionally sandwiched between the pedal body and the cleat, or sandwiched between a cleat-receiving member fastened to the pedal body and the pedal body, the cleat receiving member having grooves or tabs for receiving the cleat. The static pre-load may be applied by fasteners, or by other clamping means.

Applications include bicycling, including racing, mountain biking, and stationary bicycles. Applications also include other stationary exercise equipment having pedals or footpads, elliptical exercise equipment, and running or walking where the shoe is configured with an internal force sensor of the invention. The ability to detect excursion of the sensor output to a "negative" value by pre-stressing the force sensor layer is of use in more accurately analyzing gait. Applications for cross-country skiing, rowing, sculling or training for other sports are also envisaged.

The invention is also a method for calculating individual power output during an athletic activity, which comprises the acts of sensing pressure at a particular location in a mechanical stack via a force sensing layer, wherein the particular location is related to the athletic activity; converting an analog signal generated in the force sensing layer to a digital signal; computing power as a function of time by application of a mathematical algorithm applied to the signal; and displaying power to a user in a manner that allows the user to view the power while performing the athletic activity, where the power sensor is pre-loaded under a fixed compression so that both positive and negative force excursions from a static or resting state can be measured. By conveying the digital signal wirelessly to the display, the user is free to position the display where most convenient, for example on a handlebar or non-moving part of a bicycle, or on a wrist or headband.

In another embodiment, the invention is a method of dynamically bracketing a metric during an athletic activity, which comprises the acts of providing a power monitor of the invention to user performing an athletic activity that affects at least one of heart rate, power output, muscle fatigue, and body heat; wherein the power monitor is configured for a) continuously measuring a metric during the performance of the athletic activity, wherein the metric is associated with at least one of the performance level of the user at the athletic activity and the exertion level of the user, b) for receiving a bracket request from the user at a particular time during the performance of the athletic activity, and c) for assigning a bracket of metric values corresponding to a set of values substantially centered around the measured metric value at the particular time at which the bracket request was received. The method further may comprise a step for alerting the user if the user falls outside of the assigned bracket of metric values.

Thus, as discussed herein, the embodiments of the present invention relate to a system of power output measurement for bicycling, but the invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes that come within the meaning and range of equivalency of the claims are to be embraced within their scope.

We claim:

1. A power monitor for measuring performance of a bicyclist, which comprises:
   a mechanical linkage for linking a driver shoe member, said driver shoe member having a sole, to a driven member, wherein said driven member is configured for interlockingly engaging a pedal operatively attached to a crank of a bicycle;
   said mechanical linkage comprising a force sensor layer configured for interfacing between said driver shoe member and said driven member, said force sensor layer having an output analog signal;
   further characterized in that said force sensor layer is pre-stressed by a static compressive load, such that a deformation of said force sensor layer under a dynamic compressive load is detected as a positive change in said output analog signal and a deformation of said force sensor under a dynamic decompressive load is detected as a negative change in said output analog signal, said output analog signal at rest being non-zero.

2. The power monitor of claim 1, wherein said mechanical linkage further comprises at least one threaded fastener for attaching a cleat with cleat body to a mounting interface on said sole of said driver shoe member, wherein said force sensor layer is sandwiched between said mounting interface and said cleat body.

3. The power monitor of claim 2, wherein said force sensor layer is pre-stressed by a torque applied to said at least one threaded fastener.

4. The power monitor of claim 2, wherein said force sensor layer is directly attached to said cleat body.

5. The power monitor of claim 1, wherein said force sensor layer is directly attached to said sole of said shoe.

6. The power monitor of claim 1, wherein said force sensor layer comprises a sheet of a force sensing resistor material.

7. The power monitor of claim 1, further comprising a sensor assembly, said sensor assembly comprising a sensor coverplate and a sensor baseplate, with said force sensor layer sandwiched therebetween, wherein said sensor assembly is removable from said driver shoe member.

8. The power monitor of claim 1, further comprising a sensor circuit for applying a voltage or a current to said force sensor layer.

9. The power monitor of claim 8, wherein said sensor circuit is configured for converting said changes in said output analog signal to a measurement of the power expended in driving said driven member against a resistance for a unit of time.

10. The power monitor of claim 9, wherein said sensor circuit is configured for converting said measurement of the power expended to a digital signal and for wirelessly transmitting said digital signal to a remote signal processing and display circuit.

11. The power monitor of claim 10, wherein said signal processing and display circuit is configured for driving a graphical display of said measurement of the power expended.

12. The power monitor of claim 8, wherein said sensor circuit is configured with mounting system and housing for attaching to a shoe.

13. A shoe for bicycling, which comprises the power monitor of claim 1.

14. A shoe for bicycling, which comprises the power monitor and the cleat of claim 2.

15. The power monitor of claim 7, further comprising a means for mounting said sensor assembly to said driver shoe member, said means for mounting comprising at least one threaded fastener, wherein said force sensor layer is pre-stressed by a torque applied to said at least one threaded fastener.

* * * * *